(12) United States Patent
Van Vaals

(10) Patent No.: US 8,112,143 B2
(45) Date of Patent: Feb. 7, 2012

(54) USING MAGNETIC RESONANCE IMAGES FOR LOCATING ANATOMICAL TARGETS

(75) Inventor: Johannes Jacobus Van Vaals, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1092 days.

(21) Appl. No.: 10/567,200

(22) PCT Filed: Aug. 2, 2004

(86) PCT No.: PCT/IB2004/051355
§ 371 (c)(1),
(2), (4) Date: Feb. 3, 2006

(87) PCT Pub. No.: WO2005/016140
PCT Pub. Date: Feb. 24, 2005

(65) Prior Publication Data
US 2006/0264740 A1    Nov. 23, 2006

(30) Foreign Application Priority Data
Aug. 8, 2003   (EP) .................................... 03077523

(51) Int. Cl.
*A61B 5/055* (2006.01)
(52) U.S. Cl. ......... 600/410; 600/407; 600/414; 600/415
(58) Field of Classification Search .................. 600/407, 600/426, 427, 429, 410, 414, 415, 425; 378/63, 378/65, 205; 324/307, 309
See application file for complete search history.

(56) References Cited

U.S. PATENT DOCUMENTS

| | | | |
|---|---|---|---|
| 5,315,630 A * | 5/1994 | Sturm et al. | 378/65 |
| 5,800,353 A | 9/1998 | McLaurin | 600/407 |
| 5,894,503 A * | 4/1999 | Shepherd et al. | 378/203 |
| 6,405,072 B1 * | 6/2002 | Cosman | 600/426 |
| 6,445,182 B1 * | 9/2002 | Dean et al. | 324/309 |
| 6,466,813 B1 | 10/2002 | Shukla et al. | 600/411 |
| 6,473,634 B1 | 10/2002 | Barni | 600/425 |
| 6,795,571 B2 * | 9/2004 | Kusch | 382/131 |
| 6,865,253 B2 * | 3/2005 | Blumhofer et al. | 378/65 |
| 2002/0021128 A1 | 2/2002 | Kuhara | 324/309 |
| 2002/0085668 A1 * | 7/2002 | Blumhofer et al. | 378/68 |
| 2003/0187351 A1 * | 10/2003 | Franck et al. | 600/429 |
| 2003/0206614 A1 * | 11/2003 | Kendrick et al. | 378/205 |

FOREIGN PATENT DOCUMENTS
EP   1 220 153 A2   7/2002
* cited by examiner

Primary Examiner — Tse Chen
Assistant Examiner — Rochelle Reardon

(57) ABSTRACT

A novel MR method and system is described for using MR images for planning radiotherapy treatment. The images are obtained by a scanner which generates a magnetic field with a magnetic center (isocenter). First at least one fiducial marker (4; 5) is applied to the body (1) of the patient at a predetermined distance from the isocenter. The patient is repositioned within said scanner such that an anatomical target (2) is located in close vicinity of said isocenter. A first image of said target (2) is obtained and then the patient (1) is shifted such that the fiducial marker (4; 5) is close to the isocenter. A second image is obtained at the shifted position, in which the fiducial marker has an accurate geometrical position, that is merged into said first image.

13 Claims, 4 Drawing Sheets

USING MAGNETIC RESONANCE IMAGES FOR LOCATING ANATOMICAL TARGETS

The invention relates to a method and a system for using magnetic resonance (MR) images in radiotherapy treatment planning (RTP).

Radiotherapy treatment planning is the calculation of the delivery of a precise dose of radiation to a specific volume of tissue within the patient. Medical equipment for radiation therapy treats tumorous tissue with high energy radiation. The amount of radiation and its placement must be accurately controlled to ensure that the tumor receives sufficient radiation to be destroyed and that damage to the surrounding and adjacent nor-tumorous tissue is minimized. The high energy radiation is collimated to direct a beam into the patient to the lesion. In the case of treatment planning for external beam therapy the output of a treatment plan would normally be a schema for a determined number of external treatment beams of radiation including their cross sectional dimensions and the length of time for which they are turned on, angular orientations about the patient, angular rotation about the central beam axis, and instructions for the precise set up of these beams on the patient surface to allow the beams to intersect in the treatment volume. Specific orientations of the patient treatment couch may also be included.

Internal source radiation therapy (referred to as brachytherapy) places capsules of radioactive material inside the patient in proximity to the tumorous tissue. Dose and placement are accurately controlled by the physical positioning of the isotope. In this case, the treatment planning for intra cavity treatment, the treatment plan would include the number of radioactive sources to be inserted, their activity and the overall time for which they are inserted, their precise position within the patient and the positions of any non-radioactive spacers.

Recent advances have allowed MR images to be used as the radiotherapy treatment planning modality. Magnetic resonance imaging (MRI) is superior to computerized tomography (CT) for providing non-invasive visualization of internal anatomic structures because its scans provide higher quality definition of the anatomy and better differentiation between normal and abnormal tissue. Further, MR images can be obtained in all three standard views; i.e. front view, side view and cross-section (designated as coronal, sagittal and axial views respectively). These three views significantly improve the ability of the physician to develop a 3-dimensional comprehension of the interrelation of structures which improves diagnostic interpretation as well as therapeutic intervention. The interaction between the radiation treatment beams and the patient tissue is planned out using patient MR image data. It is most important that this image data is linear, i.e. geometrically undistorted. The use of MR in RT planning has required the development of gradient distortion correction software to impose linearity on the 3D image data set used for planning. However, the distance away from the isocenter of the field of view (FOV) at which this linearity starts to break down leads to inaccuracies in planning treatments for larger patients. In particular, radiotherapy treatment set-up requires the use of patient surface markers and these are, by definition, further away from the isocenter of the magnet when the patient is placed centrally for imaging. These are therefore susceptible to any remaining inherent image distortion.

Legal requirements for the delivery of the correct physician prescribed dose to the treatment volume result in very small tolerances in physical errors. Typically, when planning using CT slices, the planner would aim to calculate all measurements in the schema to the nearest millimeter or nearest degree. The inherent distortion in MR images therefore means that in some cases they are not suitable enough for radiotherapy treatment planning, even though MR produces superior soft tissue resolution.

U.S. Pat. No. 5,800,353 to Robert L. McLaurin, Jr. discloses a medical procedure which accepts that MR scans contain an inherent distortion, but solves the problem of how to use them for treatment planning by aligning all scans relative to a machine frame of reference. For imaging a framework over the body containing fiducial markers is used and the distortion in the resulting images is considered by analyzing the final positions of the fiducial markers in the resulting images.

U.S. Pat. No. 6,466,813 to Himanshu P. Shukla et. al. discloses the use of MR images in radiation treatment planning and includes a correction for distortion. However, it is not clearly disclosed in which way this correction for distortion is performed, and after correction the linearity at larger distance from isocenter breaks down beyond acceptable accuracy.

There is a need, therefore, for a method and system which improves accuracy in MR-based Radiation Therapy planning and simulation.

The present invention contemplates a new and improved method and a system to overcome the above mentioned problems and discloses a method by which MR images may be used in radiotherapy treatment planning using magnetic resonance image data as primary data set by repositioning of patient for higher accuracy of fiducial markers position.

To accomplish the above, using the MR acquired images exclusively, the patient is imaged with the anatomical target in the magnetic center (isocenter) of the MR system to visualize and locate the lesion or tumor. One or more fiducial markers placed on the patient away from the isocenter are imaged successively, in such a way that the marker is closer to isocenter and therefore its position is known more accurately. The accurate position of the marker is then merged into the first image. If needed, this procedure can be repeated for further fiducial markers. The accurate position of the fiducial marker can be determined by the measured shift of the patient table. On the other hand a composite image data set can be built up by merging the first and second images by overlapping corresponding parts in the images.

It is a further object of the present invention to provide a system using an open MR imager as imaging device, which permits the patient to be inserted sideways and to reposition the patient table in almost any direction.

These and other objects and advantages of the invention will become apparent to those skilled in the art upon a study of the following description and the accompanying drawings, in which.

Figure 1A:
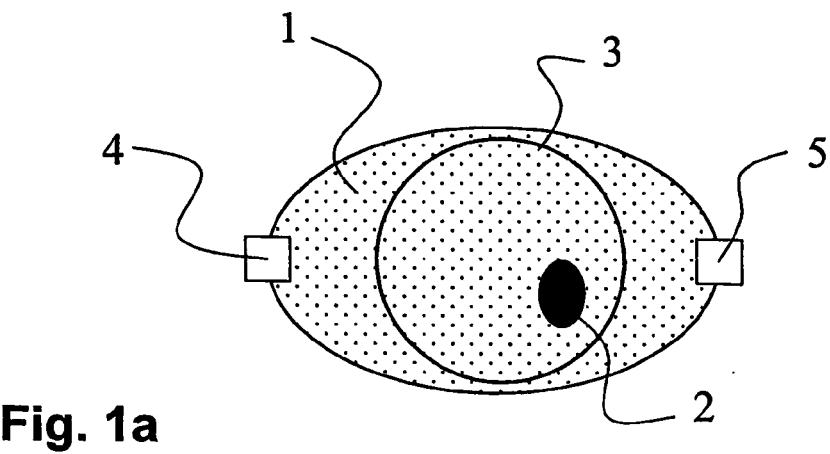
FIG. 1 shows three imaging positions of a patient for accurate geometric position
a) of lesion,
b) of a right marker and
c) of a left marker.

Image-based radiation therapy planning (RTP) requires images with as little spatial distortion as possible. During successive radiation therapy treatment sessions, the patient is positioned in the radiation therapy device using external markers, or fiducial markers, which are either semi-permanently attached or marked on the patient, or on a fixation mask or device which forces the patient into the same identical position. The spatial relation between the external, or fiducial, markers and the internal location of the lesion needs to be correct, since this is used to plan the radiation therapy. Any inaccuracies result in sub-optimal treatment, since the radiation will be focused not exactly at the actual position of the lesion.

In CT-based RTP, the spatial accuracy of the images is typically 1 to 2 mm. Recently, it has become possible to use MRI as the primary data set for RTP by using advantageously open MR systems. Open MR scanners are preferred for their patient friendliness, patient positioning flexibility, ease of patient accessibility for interventional procedures and cost effectiveness. Patient anxiety is reduced by the open design, especially for the claustrophobic patient. Technologists also benefit from the open design through ease of patient positioning and more friendly, direct patient communications. With open systems, image quality has also benefited from the patient positioning flexibility because images can always be collected at or near the magnetic center (isocenter). Since especially gradient non-linearity leads to distorted images, a special gradient distortion correction (gdc) software correction is applied to improve the accuracy. However, for larger patients the accuracy at greater distance from the isocenter is not sufficient. The resulting errors in the measured position of external markers can become unacceptable. With the proposed inventive method, this error can be reduced allowing improved accuracy and wider use of MRI for RTP.

To reduce the errors due to image distortion, the patient is imaged in two or more positions. First, the patient is imaged with the lesion approximately in the isocenter of the MR system. In these images, some or all markers may be so far from the isocenter, that even with gradient distortion correction, the geometrical position of the markers is measured not accurate enough, i.e. the markers depicted on the original image with the large FOV do not correspond exactly with the real positions of the markers. Thus, the positions of markers (4,5,6,7,8,9,10,11) of the patient 1 are detected incorrectly. In order to correct this mistake, the patient is imaged in at least one additional position, with the patient off-center in such a way that the markers on one side will be closer to the isocenter and therefore can be measured more accurately. If needed, this can be repeated moving the patient the other way for markers on the other side of the patient. So, the patient is shifted to successive positions relative to the isocenter and, thereby shifting the regions of interest relative to the imaging FOV. The shift of the patient table relative to the isocenter determines the accurate geometrical position of the external or fiducial markers (4,5,6,7,8,9,10,11), which positions are merged into the image with the large FOV. This is accomplished e.g. by shifting the fiducial markers (4,5,6,7,8,9,10, 11) to the correct positions. On the other hand a composite image data set can be created from the acquired data taken from the various regions of interest across the patient by merging the images by overlapping corresponding parts with accurate geometrical positions of the images.

Figure 1B:
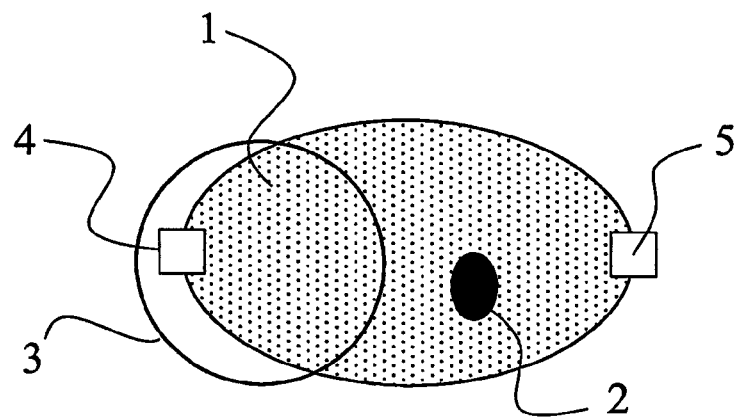
Figure 1C:
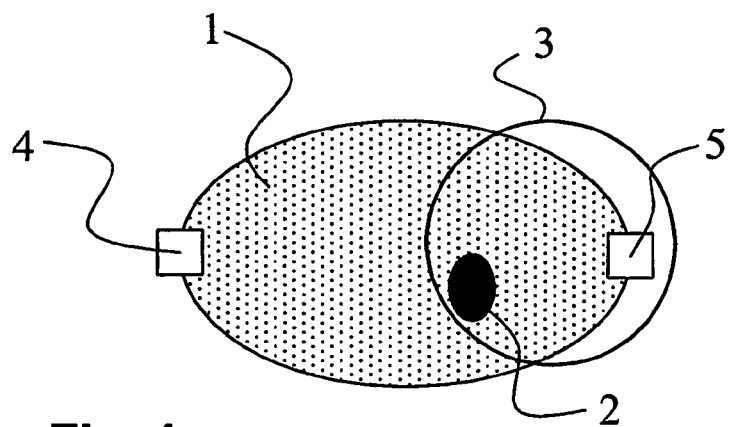

FIG. 1 depicts the above described situation. Three imaging positions of a large patient 1 having a lesion 2, are schematically shown. The ellipse represents an MR image of a large person 1. On the left side and on the right side of the patient external or fiducial markers 4,5, drawn as small squares, are fixed on the patient 1. These external or fiducial markers can also be fixed on a fixation device. The circle represents the optimal field of view $FOV^{opt}$ 3 wherein the geometrical accuracy of the imaging system is acceptable, i.e. has a prescribed tolerance. For example, the requirement of a prescribed tolerance could mean only using those parts of the image where the distortion produces an inaccuracy in the identification of the position of structures of less than 1 mm or even of, say, less than 0.5 mm or of less than 0.25 mm. Using the image portions within an identified $FOV^{opt}$ with such a prescribed tolerance allows the parts of the image which contain minimal distortion of the relative positions of anatomical structures to be used to provide information for the radiotherapy, or RT, planning process. The radius of the circle represents the distance from the isocenter at which the linearity starts to break down. The whole imaging field of view FOV of the MR image is larger than the $FOV^{opt}$ 3 and usually comprises the total image of the lesion 2 and the fiducial markers 4,5. FIG. 1a shows the patient 1 positioned with its lesion 2 near to the isocenter of the MR apparatus. Both fiducial markers 4,5 are out of the boundary of $FOV^{opt}$ 3. That means that the geometrical position of the lesion 2 is very accurate, but the markers 4,5 are in the FOV where image distortion is inevitable, even by applying of gradient distortion correction software, and their geometrical position is inaccurate. In such a manner the fiducial markers are not usable for RTP. FIG. 1b shows the patient 1 positioned with its right fiducial marker 4 within the $FOV^{opt}$ 3 and the lesion 2 near to the margin of the $FOV^{opt}$ 3. This position gives an accurate geometrical position in the MR image for the right marker 4 and FIG. 1c shows the patient 1 positioned with its left fiducial marker 5 and lesion 2 within the $FOV^{opt}$. The shifts of the patient can be measured to determine the correct geometric position of the markers. These imaging positions with its accurate geometric positions of lesion 2 and fiducial markers 4,5 are merged in the image acquired with the lesion 2 positioned close to the isocenter (FIG. 1a). Thus, the images with the optimal FOV in FIGS. 1a to 1c are merged to a single image. On the other hand the images with the accurate geometrical positions of the fiducial markers 4, 5 can also be merged in the image with large FOV, wherein the lesion 2 is imaged in close vicinity of the isocenter.

Figure 2A:
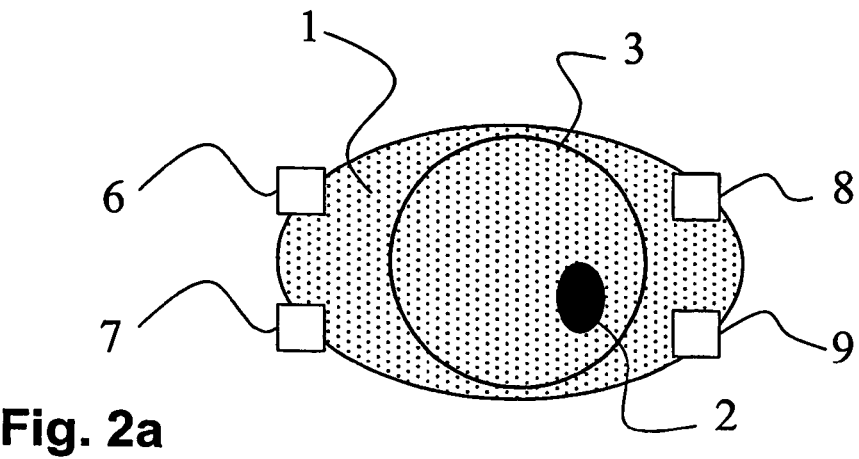
FIG. 2 shows three imaging positions of a patient for accurate geometric position
a) of lesion,
b) of a right anterior and posterior marker and
c) of a left anterior and posterior marker.
Figure 2B:
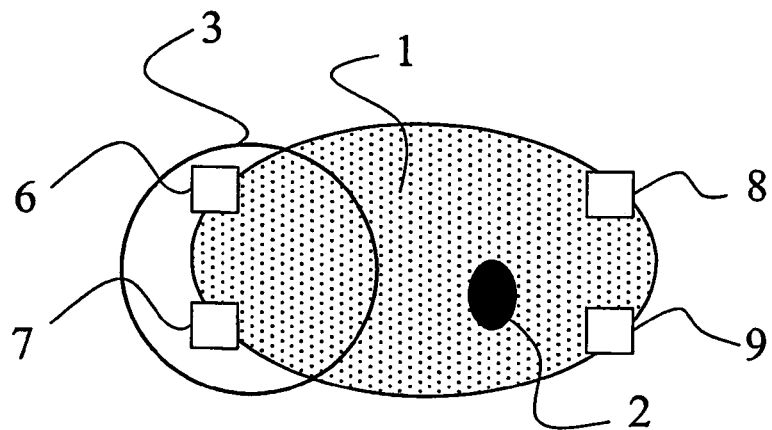
Figure 2C:
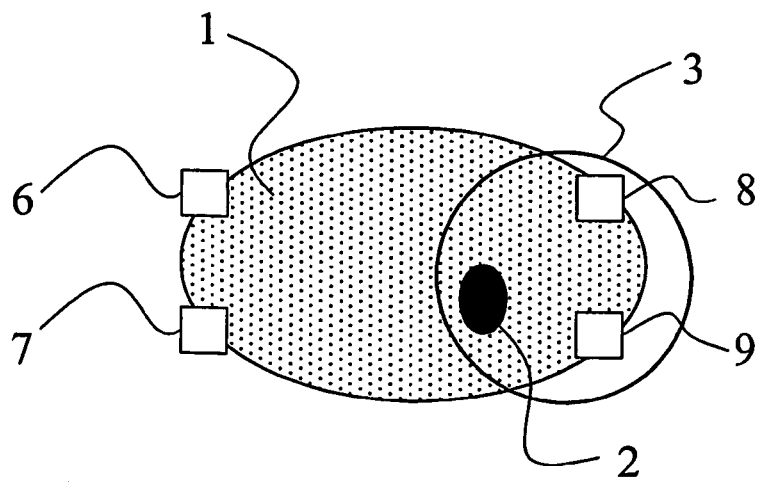

FIG. 2 shows three imaging positions of a large person 1, using four fiducial markers, namely on both sides anterior and posterior. FIG. 2a depicts the patient 1 positioned with its lesion 2 near to isocenter and all fiducial markers 6,7,8,9 are out of the boundary of $FOV^{opt}$ 3. The geometrical position of the lesion 2 is very accurate, but the geometrical positions of the markers 6,7,8,9 are inaccurate. FIG. 2b shows the patient 1 shifted left and positioned with its right posterior and anterior fiducial markers 6,7 within the $FOV^{opt}$ 3 and the lesion 2 near to the margin of the $FOV^{opt}$ 3 and FIG. 2c shows the patient 1 shifted right and positioned with its left posterior and anterior fiducial markers 8,9 and lesion 2 within the $FOV^{opt}$. These imaging positions permit, as previously described, the merging of accurate representations of the geometric positions of the fiducial markers 6,7,8,9 in FIG. 2a.

Figure 3A:
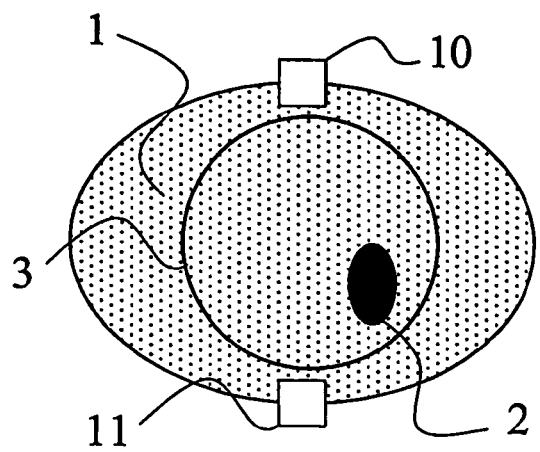
FIG. 3 shows three imaging positions of a patient for accurate geometric position
a) of lesion,
b) of an anterior marker and
c) of a posterior marker.
Figure 3B:
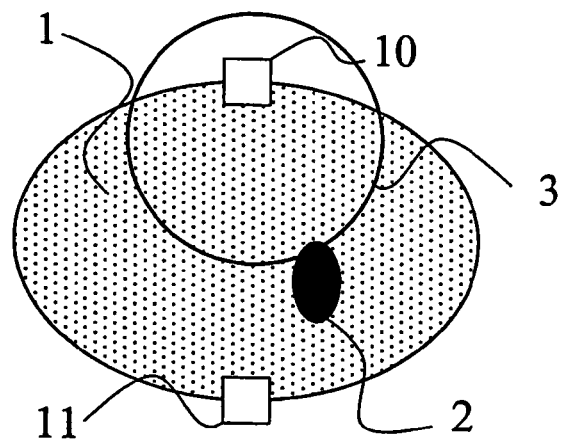
Figure 3C:
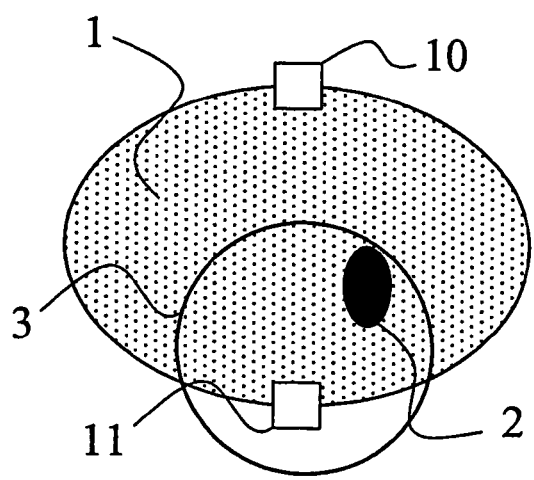

FIG. 3 shows three imaging positions of a large person 1, using two fiducial markers, namely anterior and posterior. FIG. 3a depicts the patient 1 positioned with its lesion 2 near to isocenter and all fiducial markers 10,11 are out of the boundary of $FOV^{opt}$ 3. The geometrical position of the lesion 2 is very accurate, but the geometrical positions of the markers 10,11 are inaccurate. FIG. 3b shows the patient 1 shifted down and positioned with its anterior fiducial marker 10 within the $FOV^{opt}$ 3 and the lesion 2 near to the margin of the $FOV^{opt}$ 3 and FIG. 3c shows the patient 1 shifted up and positioned with its posterior fiducial marker 11 and lesion 2 within the $FOV^{opt}$. These imaging positions permit, as described above, the merging of accurate representations of the geometric positions of the fiducial markers 10, 11 in FIG. 3a.

The drawings show fiducial markers 4,5,6,7,8,9,10,11 placed laterally (left and right), anterior or posterior on the patient. These markers may also be placed on the patient or be fixed on a fixation device at other positions, e.g. on the midline of the patient, which runs from head to feet. The point is to have fiducial markers at positions which can be positioned within the area close to the isocenter of the magnet where the position measured in the MR images is still accurate. For not too large patients, midline markers as mentioned above, will be possible—either because this position will be within the $FOV^{opt}$ or because the patient is moved higher or lower so that it is. However for very large patients, midline markers will be relatively far from the isocenter and cannot in such a situation be measured accurately, because the magnet bore or magnet gap limits the possible offset in the anterior direction.

It is now clear how the creation of a composite image can be achieved by overlapping the corresponding parts of the acquired images. The merging of the images can be achieved by registering the portions of the images which correspond to each other. For example, a composite image can be formed from the merging, or registration, of the three $FOV^{opt}$ 3 sections shown in FIGS. 1a, 1b and 1c. The $FOV^{opt}$ from FIG. 1a will have an overlapping area with the $FOV^{opt}$ from FIG. 1b, the overlapping areas in common being respectively on the right hand side of $FOV^{opt}$ in FIG. 1a and on the left hand side of $FOV^{opt}$ in FIG. 1b. These two sections represent the same anatomical parts. Registration techniques can be used to register these two overlapping areas with each other and thus bring the two $FOV^{opt}$ sections from image 1a and 1b into line with each other. Similarly, the $FOV^{opt}$ from FIG. 1a will have an overlapping area with the $FOV^{opt}$ from FIG. 1c, the overlapping areas in common being respectively on the left hand side of $FOV^{opt}$ in FIG. 1a and on the right hand side of $FOV^{opt}$ in FIG. 1c. Again, registration techniques can be used to register these two overlapping areas with each other, thus bringing the two $FOV^{opt}$ sections from image 1a and 1c into line with each other. If all such corresponding overlapping areas in all $FOV^{opt}$ sections are registered, or merged, in this way then a composite image will result.

With an open MRI system, images of lesion 2 can always be collected at or near the isocenter. This system permits to enter the patient into the MR device sideways. For this purpose the system comprises a patient table which permits to reposition the patient 1 in the left-right direction within the open MRI. With this patient table it is possible to bring the fiducial markers 4; 5; 6; 7; 8; 9, which are fixed to the patient or on a fixation device, successively within the $FOV^{opt}$ 3 as near as possible to the isocenter of the MR system. When the patient is moved up or down, also markers 10,11 can be moved and positioned within the $FOV^{opt}$ 3. Further a software may be applied which is called Gradient Distortion Correction (GDC) to correct images for gradient-induced distortion. This leads to accurate images of the open MR system within the mentioned $FOV^{opt}$ 3.

The fiducial marker position, which is, thanks to the displacement, moved within the $FOV^{opt}$ 3 therefore can be accurately determined by measuring the shift of the patient with reference to the position with lesion 2 in the isocenter position. The images of these positions should be merged with the image acquired with the lesion 2 positioned close to the isocenter to create images with accurate positions of fiducial markers. This can be achieved simply by correcting the positions of the markers in the image obtained in the position depicted in FIGS. 1a, 2a, or 3a, respectively. For example, this can be done by using the measured shift, or displacement, of the position of the patient when translating the patient from the patient position at which the image of the lesion was acquired to the patient position at which the image of the fiducial marker was acquired. For example, the patient is first positioned and an image of the lesion is acquired showing a central reference point, as is known. The patient is then shifted a number of centimeters to the right before the acquisition of an image of a fiducial marker. The image containing the fiducial marked in an undistorted portion of the image also contains a central reference point. The numerical value of the physical shift undergone by the patient is the distance in reality between the two central reference points in the two images. If the accurate position of the fiducial marker can know by deduced from the second image, it's actual position in the first image, that of the lesion, can be calculated. The first image can then be corrected. Alternatively, the process can be performed the other way around, with the position of the lesion, or region of interest, being corrected in the image which carries accurate positional information about the fiducial markers. Alternatively, the images can be merged where a composed image is created primarily from the parts of the images covered by the $FOV^{opt}$ 3 as measured in positions 1a, 1b,1c, or 2a,2b,2c, or 3a,3b,3c, respectively. This merging of images can be performed using image registration techniques.

With the proposed method and system, geometrical positions of a lesion 2 and fiducial markers can be determined accurately which is also allowing improved accuracy and wider use of magnetic resonance imaging (MRI), especially for open MRI in radiotherapy treatment planning and simulation, where the exact location and extent of the tumor needs to be known as good as possible. However, also a closed MR system with a main magnet with a large bore can be used, provided that the patient support can be moved sideways and/or up and down.

Figure 4:
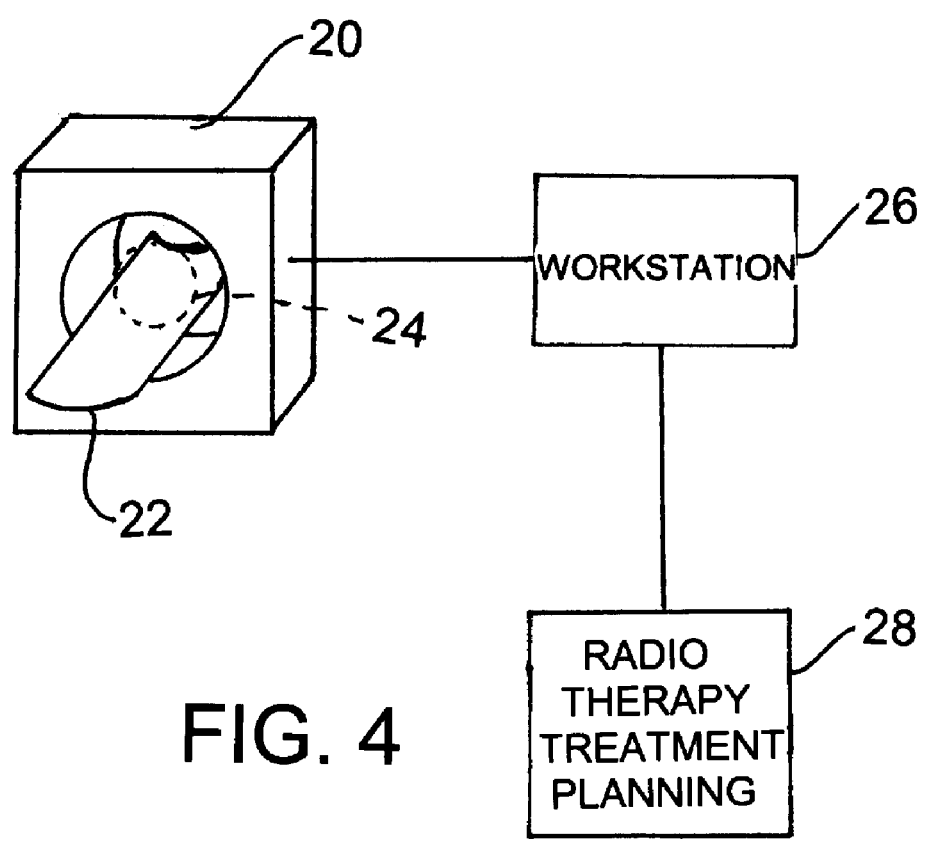
FIG. 4 shows a magnetic resonance imaging system.

With reference to FIG. 4, the invention can be advantageously utilized in practice by first performing the acquisition of the magnetic resonance images using a magnetic resonance imager 20 with a patient table, patient bed or other patient support means 22 which can be translated or shifted relative to the isocenter 24 of the magnetic field. Fiducial markers, otherwise known as external markers or surface markers, are placed on the surface of the patient. The patient is positioned on the patient table or other support means and positioned for the initial image. This may be the image acquired with the lesion, or region of interest, positioned close to the isocenter of the magnetic field, or at least positioned in the $FOV^{opt}$, or optimal field of view, of the magnetic field. This initial image is acquired. The position of the patient is then shifted, or displaced, to another position in which one of the fiducial markers is positioned close to the isocenter of the magnetic field, or at least positioned in the $FOV^{opt}$. The second image is then acquired. Further shifts are performed and further images are acquired until all fiducial markers and the region of interest, or lesion, are represented in a $FOV^{opt}$ of an image. It will be obvious to those skilled in the art that the order in which the images are taken is immaterial.

Following imaging the acquired images are used to form an image suitable for radiotherapy planning using the other steps of the method of the invention. The formation of such an image may take place at the controls of the magnetic resonance imager, or make take place on a separate work station 26 or may also take place in a radiotherapy treatment planning system or workstation 28. Once a suitable image is formed it is used for radiotherapy treatment planning using known treatment planning techniques.

The production of the image suitable for radiotherapy treatment planning may involve using the known shifts of the patient between images, as has been described. Image production may also involve simply merging, or registering the images as has been described. Image production may also however involve a combination of the two, for example in which the accurate positions of the fiducial markers are calculated and then used in the image containing the accurate image of the lesion to register in the accurate portions of the images containing the fiducial markers in the optimal field of view, or $FOV^{opt}$. In this case a composite view would be formed utilizing the best portions of each overall image. In fact, the single image which results, and which may then be used for radiotherapy treatment planning, may be one of the originally acquired images which has been corrected according to one of the methods described above, or, could be a new image which is a composite of portions of the original images.

The present invention is therefore not only directed to the method for using the images but also to a specific designed magnetic resonance imaging system and a computer programme for the execution of the above described method.

The computer programme is stored on a computer usable medium and is designed to use magnetic resonance images and to cause the execution of the different steps of the above mentioned method. The computer programme is particularly advantageously employed in a magnetic resonance imaging system which generates a magnetic field with a magnetic center (isocenter), as origin for locating anatomical targets in a patient, e.g. for radiotherapy. At least one fiducial marker is applied to the body of the patient at a distance from the isocenter.

It is further noted that the method according to the present invention can also be used on a workstation or a radiotherapy planning system remote from the magnetic resonance imaging system, so that the radiotherapy treatment planning can be executed, for example, in a different room, or a different hospital department, or even a different hospital.

The invention claimed is:

1. A method of magnetic resonance imaging using a magnetic resonance imaging scanner which generates a magnetic field that is more linear adjacent a magnetic isocenter and is less linear displaced from the magnetic isocenter, the method comprising:

obtaining a first magnetic resonance image of a patient including an anatomical target and at least one fiducial marker displaced from the anatomical target, the first image being obtained at a position of the patient within said scanner wherein the anatomical target is located in close vicinity to said magnetic isocenter and the at least one fiducial marker is located further from the magnetic isocenter than the anatomical target, such that a region of the first image which includes the anatomical target is less distorted than a region which includes the at least one fiducial marker;

obtaining a second magnetic resonance image of the patient including the anatomical target and the at least one fiducial marker, the second image being obtained at a shifted position of the patient within said scanner wherein the at least one fiducial marker is located in close vicinity to said magnetic isocenter and the anatomical region is located further from the magnetic isocenter than the at least one fiducial marker such that a region of the second image which includes the at least one fiducial marker is less distorted than a region which includes the anatomical target;

merging the less distorted region of the first image which includes the anatomical target and the less distorted region of the second image which includes the at least one fiducial marker into a composite image; and at least one of storing the composite image in computer memory and displaying the composite image on a monitor.

2. The method as claimed in claim 1, further including:

shifting of the patient relative to the magnetic isocenter between the first and second images and measuring the shift and wherein accurate geometrical positions of the target and the at least one fiducial marker are determined using the measured shift of the patient.

3. The method as claimed in claim 1, further including:

overlapping corresponding parts in the first and second images to form said composite image.

4. The method as claimed in claim 1, wherein a Field-of-View (FOV) is determined which has geometrical positions with a prescribed accuracy for the target in the first image and the at least one fiducial marker in the second image.

5. The method as claimed in claim 1, wherein said at least one fiducial marker is applied left and right laterally on the patient.

6. The method as claimed in claim 1, wherein said at least one fiducial marker is applied laterally on both sides anterior and posterior on the patient.

7. The method as claimed in claim 1, wherein said at least one fiducial marker is applied anterior or posterior on the patient.

8. The method as claimed in claim 1, further including:

shifting the patient to locate each of a plurality of additional fiducial markers in close vicinity to the magnetic isocenter, obtaining additional magnetic resonance images with each of the additional fiducial markers in close vicinity to the magnetic isocenter, and merging the additional magnetic resonance images with the first and second images to form the composite image.

9. A magnetic resonance imaging system which generates a magnetic field with a magnetic center, as origin for locating an anatomical target in a patient wherein at least one fiducial marker is configured to be placed on the patient, the magnetic resonance imaging system comprising:

a magnetic resonance scanner; and a workstation programmed to:

control the magnetic resonance scanner to acquire a first magnetic resonance image of an anatomical target and at least one fiducial placed on the patient displaced from the anatomical target, the anatomical target being located at a more geometrically accurate position and the at least one fiducial being located at a less geometrically accurate position, such that in the first magnetic resonance image, the anatomical target is depicted with greater geometric accuracy than the at least one fiducial;

control the magnetic resonance scanner to acquire a second magnetic resonance image at a shifted position relative to the first magnetic resonance image, the fiducial marker being located at the more geometrically accurate position and the anatomical target being located at the less geometrically accurate position, such that in the second magnetic resonance image, the fiducial is depicted with greater geothermic accuracy than the anatomical target;

wherein a region of the first magnetic resonance image which includes the anatomical target is less distorted than a region which includes the at least one fiducial marker and a region of the second magnetic resonance image which includes the at least one fiducial marker is less distorted than a region which includes the anatomical target;

merge the less distorted region of the first image which includes the anatomical target and the less distorted region of the second image which includes the at least one fiducial marker into a composite image.

10. The magnetic resonance imaging system as claimed in claim 9, further comprising:

a patient table which permits repositioning of the patient in the left-right direction to bring various regions of interest across the patient in close vicinity of a magnetic center of magnetic field of the magnetic resonance imager.

11. The system as claimed in claim 9, wherein the accurate geometrical position is closely adjacent a magnetic isocenter.

12. A method comprising:

generating a magnetic field with an MR scanner having a magnetic isocenter, a field-of-view (FOV) surrounding the isocenter and sized to have a geometrical accuracy within a preselected tolerance;

applying at least one fiducial marker to a body of the patient at a distance from an anatomical target;

obtaining a first MR image of the patient at a first position in which the anatomical target is positioned within the FOV;

obtaining a second MR image of the patient at a second position in which the fiducial marker is positioned within the FOV, the second position being shifted relative to the first position;

wherein a target region of the first MR image which includes the anatomical target is less distorted than a fiducial region of the first MR image which includes the fiducial marker and a the fiducial region of the second MR image which includes the fiducial marker is less distorted than the largest region of the second MR image which includes the anatomical target;

merging the less distorted region of the first image which includes the anatomical target and the less distorted region of the second image which includes the at least one fiducial marker into a composite image, and at least one of storing and displaying the composite image.

13. A system comprising:

a non-transitory computer readable medium carrying software which controls one or more computers to perform the steps of:

receiving a first MR image of a patient in a first position in which an anatomical target is within a FOV which is sufficiently adjacent an isocenter of a magnetic field used to generate the first MR image to have a preselected geometrical accuracy;

receiving a second MR image of the patient in a second position in which a fiducial marker is within the FOV, the second position being shifted relative to the first position;

wherein a region of the first magnetic resonance image which includes the anatomical target is less distorted than a region which includes the at least one fiducial marker and a region of the second magnetic resonance image which includes the at least one fiducial marker is less distorted than a region which includes the anatomical target;

merging the less distorted region of the first image which includes the anatomical target and the less distorted region of the second image which includes the fiducial marker into a composite image.

* * * * *